United States Patent
Lechleiter

(10) Patent No.: US 7,481,747 B2
(45) Date of Patent: Jan. 27, 2009

(54) METHOD AND TOOL FOR FITTING A BICYCLE

(76) Inventor: Steven R. Lechleiter, 6252 SW. 155th Ave., Beaverton, OR (US) 97007

( * ) Notice: Subject to any disclaimer, the term of this patent is extended or adjusted under 35 U.S.C. 154(b) by 140 days.

(21) Appl. No.: 11/559,623

(22) Filed: Nov. 14, 2006

(65) Prior Publication Data
US 2007/0111863 A1 May 17, 2007

Related U.S. Application Data

(60) Provisional application No. 60/736,265, filed on Nov. 14, 2005.

(51) Int. Cl.
*A63B 69/16* (2006.01)
*A63B 21/002* (2006.01)

(52) U.S. Cl. .............. 482/57; 482/91; 482/907

(58) Field of Classification Search .............. 482/57, 482/125, 91, 907
See application file for complete search history.

(56) References Cited

U.S. PATENT DOCUMENTS

| | | | | |
|---|---|---|---|---|
| 4,057,246 A | * | 11/1977 | Wilson | 482/125 |
| 4,121,827 A | * | 10/1978 | Weider | 482/125 |
| 4,245,840 A | * | 1/1981 | Van Housen | 482/124 |
| 4,665,928 A | | 5/1987 | Linial et al. | |
| 4,909,505 A | * | 3/1990 | Tee | 482/129 |
| 5,122,107 A | | 6/1992 | Gardner | |
| 5,318,494 A | * | 6/1994 | Santighian | 482/125 |
| 5,328,433 A | | 7/1994 | Berman | |
| 5,342,274 A | | 8/1994 | Hunker | |
| 5,518,486 A | * | 5/1996 | Sheeler | 482/131 |
| 5,588,444 A | | 12/1996 | Petragallo | |
| 5,813,954 A | * | 9/1998 | Wilkinson | 482/124 |
| 5,839,999 A | | 11/1998 | Pflugner | |
| 5,857,945 A | * | 1/1999 | Papp et al. | 482/124 |
| 6,423,015 B1 | | 7/2002 | Winkenbach et al. | |
| 6,450,930 B1 | * | 9/2002 | Kroke | 482/121 |
| 6,470,591 B2 | | 10/2002 | Rutkowski | |
| 6,834,436 B2 | | 12/2004 | Townsend et al. | |
| 6,921,354 B1 | | 7/2005 | Shifferaw | |

FOREIGN PATENT DOCUMENTS

WO     WO 2005084543 A1 *   9/2005

* cited by examiner

*Primary Examiner*—Loan H Thanh
*Assistant Examiner*—Allana Lewin
(74) *Attorney, Agent, or Firm*—John Smith-Hill; Smith-Hill and Bedell

(57) ABSTRACT

A tool for fitting a bicycle to a cyclist includes first and second stirrup elements, a handle, and attachment elements attaching the first and second stirrup elements to each other and to the handle. The cyclist may be positioned with the cyclist's back against a substantially flat surface and one leg extended away from the substantially flat surface and the foot of that leg engaging the first stirrup element and with the other leg bent and the foot of that leg engaging the second stirrup element. The cyclist may grasp the handle and pull the first stirrup element towards the cyclist's head to a position in which the cyclist's lumbo/sacral spine area moves away from the substantially flat surface.

6 Claims, 3 Drawing Sheets

METHOD AND TOOL FOR FITTING A BICYCLE

CROSS REFERENCE TO RELATED APPLICATION

This application claims benefit of U.S. Provisional Application No. 60/736,265 filed Nov. 14, 2005, the entire disclosure of which is hereby incorporated by reference herein for all purposes.

BACKGROUND OF THE INVENTION

This invention relates to a method and tool for fitting a bicycle to a cyclist, and in particular for assisting in selecting handlebar height relative to saddle height.

As used in this specification and in the appended claims, the term "bicycle" or "bike" means an upright pedal bicycle as distinct both from a recumbent pedal bicycle and from a motorcycle or a motor-assisted pedal cycle (moped).

Proper fitting of a bicycle to the cyclist is important to maximize the cyclist's performance and comfort and minimize the risk of injury. Fitting a bicycle to the cyclist involves selecting frame size and crank arm length based on static measurements of the cyclist's anatomy, typically taken when standing, then adjusting saddle height, saddle angle and saddle fore/aft position, and finally adjusting handlebar height, reach and angle. It is, however, recognized that it is desirable that adjustments should also be based on the cyclist's flexibility, and professional bike fitters will adjust the bike based on the cyclist's flexibility. However, the services of a professional bike fitter are expensive and accordingly many cyclists forgo the added comfort that can be achieved by flexibility-based adjustment.

A major factor affecting performance of a cyclist is wind resistance. Generally, when the bicycle has been adjusted to set the saddle at the proper height, performance is increased by lowering the handlebars relative to the saddle, since wind resistance is then reduced. Clearly, lowering the handlebars at a given saddle height results in lowering the shoulders of the cyclist relative to the pelvis. In principle, wind resistance would be minimized if the shoulders were at the same height as the pelvis so that the spine was generally horizontal (assuming horizontal travel of the bicycle). However, in order for the spine to be horizontal, the lower back must be horizontal and with a conventional saddle, having a horizontal upper surface, discomfort on the saddle will often result if the inclination of the lower back from vertical is excessive.

The present invention is concerned with facilitating a proper adjustment of handlebar height. If the handlebars are too low relative to the saddle, the cyclist's spine will be curved convexly upward, or hunched, and the cyclist may suffer from lower back pain or discomfort as a result. In addition, hunching of the back may impair breathing capacity. To avoid excessive hunching of the back, the upper part of the thoracic spine should be properly oriented with respect to the lower back (the lumbo/sacral spine). In addition, the cyclist may suffer neck discomfort as a result of lifting his head to look ahead in the direction of travel. If the handlebars are too high, performance may suffer. It is therefore desirable that the handlebars should be low, but not so low as to result in discomfort. The present invention may allow the cyclist to achieve an initial set up for the bicycle, without need for assistance from a professional bike fitter, such that the cyclist can operate at maximum performance (i.e. minimum wind resistance) without discomfort.

SUMMARY OF THE INVENTION

According to a first aspect of the present invention there is provided a tool for fitting a bicycle to a cyclist, comprising a first stirrup element, a second stirrup element, a handle, and attachment elements attaching the first and second stirrup elements to each other and to the handle, whereby the cyclist may be positioned with the cyclist's back against a substantially flat surface and one leg extended away from the substantially flat surface and the foot of that leg engaging the first stirrup element and with the other leg bent and the foot of that leg engaging the second stirrup element, and the cyclist may grasp the handle and pull the first stirrup element towards the cyclist's head to a position in which the cyclist's lumbo/sacral spine area moves away from the substantially flat surface.

According to a second aspect of the present invention there is provided a method of measuring hip flexion, including positioning oneself on a substantially flat surface, engaging one's right foot with a first stirrup element of a tool that also comprises a second stirrup element, a handle, and attachment elements attaching the first and second stirrup elements to each other and to the handle, engaging one's left foot with the second stirrup element, positioning oneself so that one's back is against the substantially flat surface, the right leg is substantially fully extended and is directed away from the substantially flat surface, the left leg is bent, and the left foot is adjacent the right calf, grasping the handle and pulling the handle towards one's chest while the right leg remains straight and the first stirrup element moves towards one's head to a position in which one's lumbo/sacral spine area moves away from the substantially flat surface, and measuring the hip flexion.

According to a third aspect of the present invention there is provided a method of measuring hip flexion, including providing a tool that comprises a first stirrup element, a second stirrup element, a handle, and attachment elements attaching the first and second stirrup elements to each other and to the handle, positioning the cyclist so that the cyclist's back is against a substantially flat surface, one leg is extended away from the substantially flat surface, the foot of said one leg engages the first stirrup element, the other leg is bent, and the foot of said other leg engages the second stirrup element, grasping the handle and pulling the handle towards the cyclist's chest while said one leg remains straight and the first stirrup element moves towards the cyclist's head to a position in which the cyclist's lumbo/sacral spine area moves away from the substantially flat surface, and measuring the cyclist's hip flexion.

According to a fourth aspect of the present invention there is provided a method of fitting a bicycle to a cyclist, including providing a tool that comprises a first stirrup element, a second stirrup element, a handle, and attachment elements attaching the first and second stirrup elements to each other and to the handle, positioning the cyclist so that the cyclist's back is against a substantially flat surface, one leg is extended away from the substantially flat surface, the foot of said one leg engages the first stirrup element, the other leg is bent, and the foot of said other leg engages the second stirrup element, grasping the handle and pulling the handle towards the cyclist's chest while said one leg remains straight and the first stirrup element moves towards the cyclist's head to a position in which the cyclist's lumbo/sacral spine area moves away from the substantially flat surface, measuring the cyclist's hip flexion, in the event that the cyclist's hip flexion is in the range from about 130° to about 140°, adjusting the bicycle so that the top of the handlebars is level with the saddle, in the event that the cyclist's hip flexion is greater than about 140°, adjusting the bicycle so that the top of the handlebars is higher than the saddle, and in the event that the cyclist's hip flexion is smaller than about 130°, adjusting the bicycle so that the top of the handlebars is lower than the saddle.

BRIEF DESCRIPTION OF THE DRAWINGS

For a better understanding of the invention, and to show how the same may be carried into effect, reference will now be made, by way of example, to the accompanying drawings, in which.

DETAILED DESCRIPTION

Figure 1:
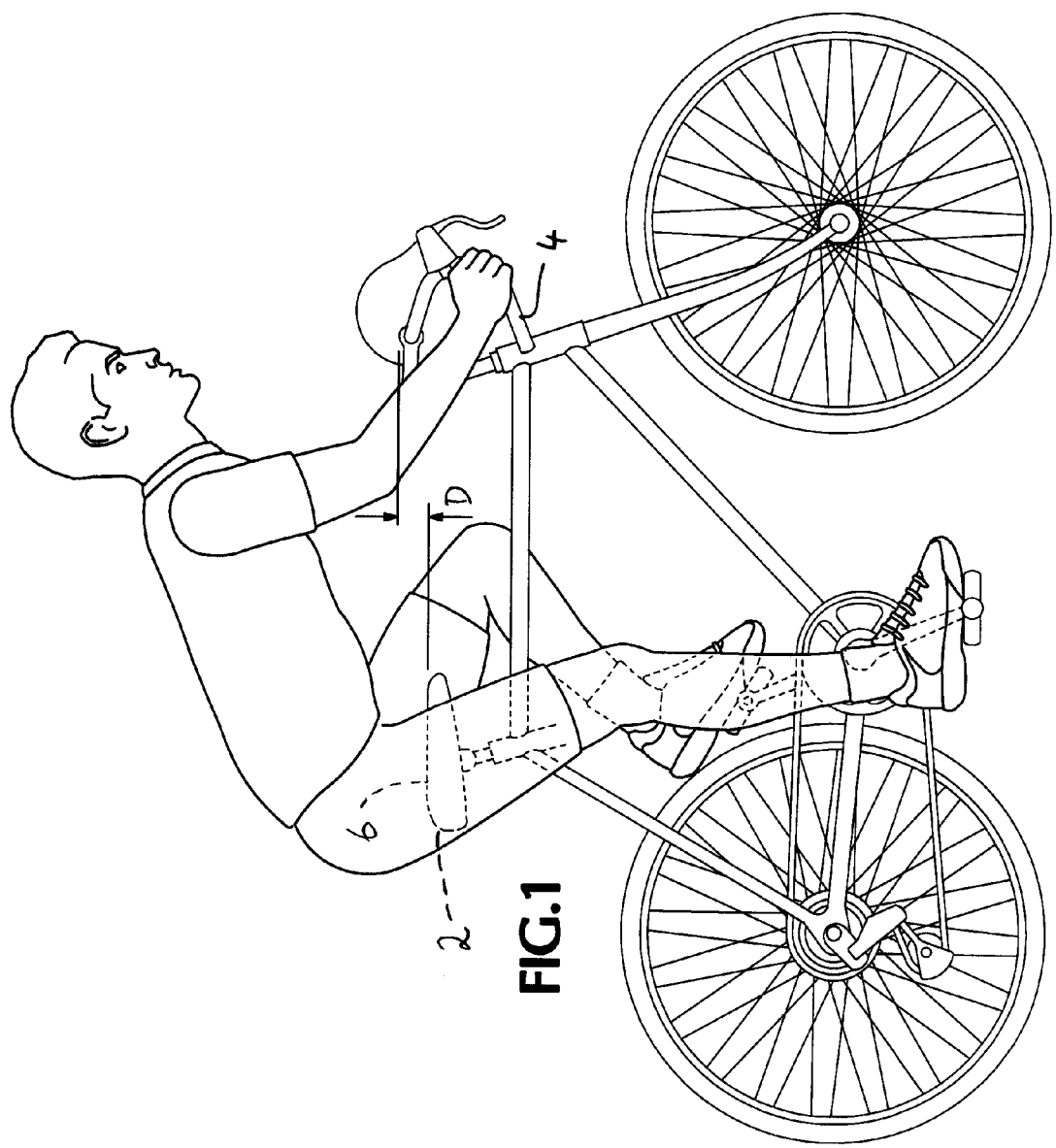
FIG. 1 is a side elevation, partly in phantom, of a cyclist on a bicycle.

FIG. 1 illustrates a bicycle having a saddle 2 and drop handlebars 4. The saddle has a generally horizontal top surface 6 at a vertical distance D from the top of the handlebars. The proper value of the distance D depends not only on static anatomical measurements, such as arm length, but also hip flexion (sometimes known as pelvis tilt), which is the angular extent to which the general alignment of the leg can deviate from the general alignment of the lower back when at least one leg is straight. It will be understood that the smaller the hip flexion angle, the greater the flexibility of the cyclist.

Figure 2:
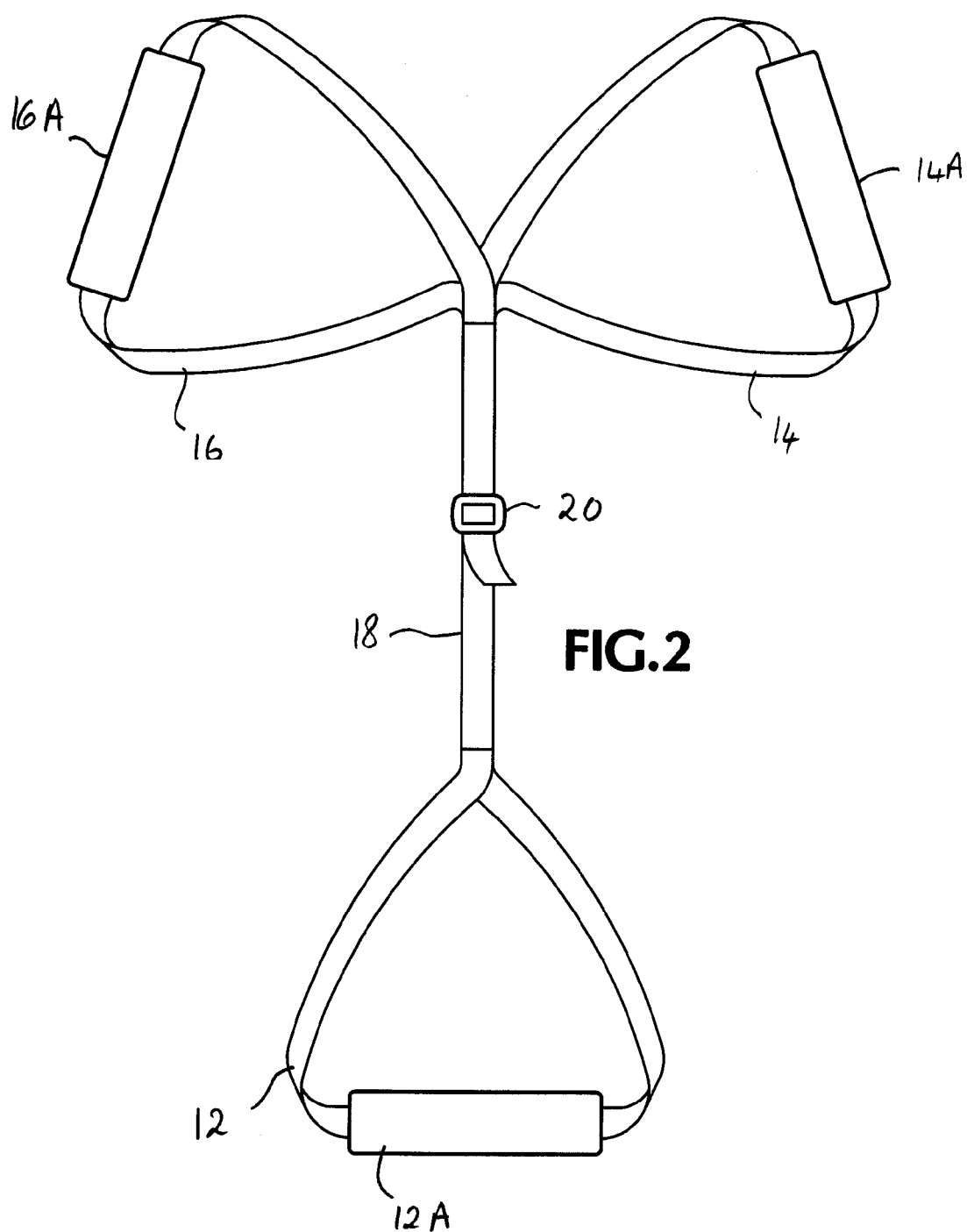
FIG. 2 illustrates a tool embodying the present invention.

FIG. 2 illustrates a tool for use in measuring hip flexion of a cyclist. The tool comprises a length of webbing that is formed to provide three loops 12, 14, 16, two of which are provided with stirrup bars 12A, 14A while the third is provided with a hand grip 16A. Each stirrup bar comprises a length of plastic pipe approximately 11 cm in length and the hand grip comprises a similar length of plastic pipe provided with a foam rubber sleeve to facilitate gripping of the pipe. The loop 12 is connected to one end of a connecting strip 18 and the loops 14 and 16 are connected to the opposite end of the connecting strip. The size of the loops and the length of the connecting strip 18 allows the stirrup bars to be at a distance of from about 25 cm to about 60 cm from each other when the webbing is under tension. The length of the connecting strip 18 is adjustable by a buckle 20.

Figure 3:
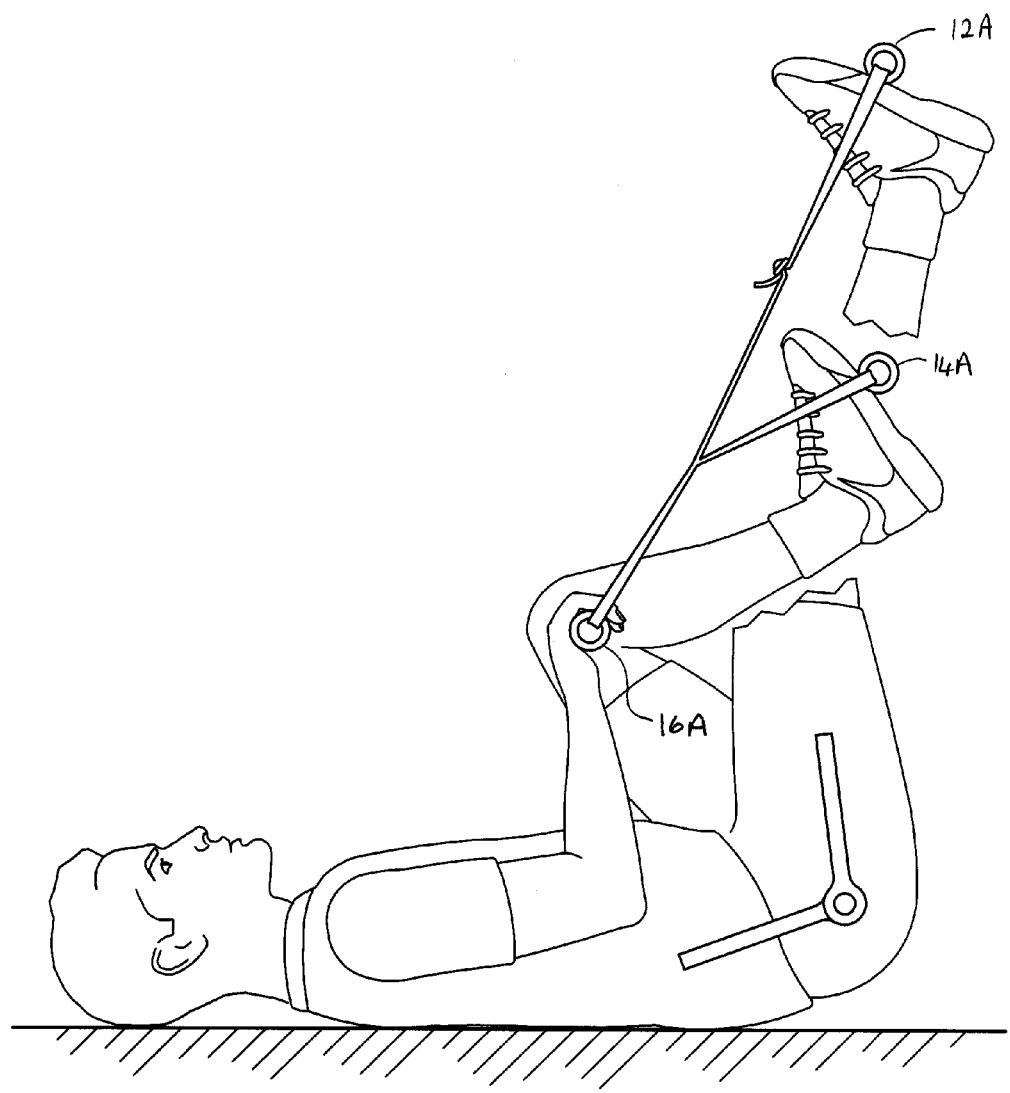
FIG. 3 is a side elevation of a cyclist using the tool shown in FIG. 2.

In the event that the loops are positioned as shown in FIG. 3, the distance between the stirrup bars may be in the range from about 25 cm to about 38 cm, depending on the position of the left foot.

In order to use the tool, the cyclist should wear snug clothing, such as the shorts and shirt that are typically worn for cycling. Initially, the cyclist places a small self-adhesive sticker at the top of his right thigh, where the femur pivots relative to the pelvis, and a second sticker at the top of the left thigh. The centers of pivotal movement of the two legs then lie on the line joining the centers of the two stickers. The cyclist places a sticker approximately 30 cm above the first sticker and a third sticker approximately 30 cm below the first sticker, so all three stickers on the right side are in a straight line. Similarly, two more stickers are applied to the left side. The three stickers on each side define two intersecting line segments. Since the three stickers on each side are initially in a straight line, the angle between the line segments is 180°.

The cyclist sets the length of the connecting strip 18 using the buckle 20 in accordance with the total length of the crank of the bicycle that is to be adjusted. The length of a commercially available crank is in the range from 165 mm to 175 mm, so the total length of the crank is from 33 cm to 35 cm.

The cyclist places his back against a flat support surface. For the sake of convenience in the following description, we will assume that the flat surface is horizontal, as shown in FIG. 3, e.g. a horizontal bench or a horizontal floor, but use of the tool is not restricted to the flat surface being horizontal. It will also be appreciated that the surface need not be completely flat and may, for example, be convexly curved to match more closely the configuration of a cyclist's back. When lying on the flat surface, the cyclist's lumbo/sacral spine area is in contact with the flat surface (through the cyclist's clothing). The cyclist grasps the hand grip 16A in both hands, positions his right foot in the loop 12, and presses lightly against the stirrup bar 12A so as to place the loops 12 and 16 and the connecting strip 18 under tension. The cyclist extends his right leg so that it is straight, positions his left foot in the loop 14, presses lightly against the stirrup bar 14A, and positions his left foot so that the ball of the left foot is adjacent the right calf. In this configuration, the central axes of the stirrup bars are parallel and are spaced at a distance corresponding to the total length of the crank of the bicycle to be adjusted. This relative positioning of the feet therefore corresponds to the relative positioning when the two feet are on the pedals of the bicycle and the right leg is fully extended, as shown in FIG. 1. While keeping the left and right feet in the same relative positions, the cyclist then pulls the hand grip towards his chest until the lumbo/sacral spine area or beltline (corresponding to the L5 vertebra) lifts off the floor. At this point, the angle between the two line segments can be measured using a goniometer or similar instrument and is the cyclist's hip flexion.

If the hip flexion angle is in the range from 130° to 140°, the initial setting for the handlebars (assuming a standard drop of about 14 cm) is that the top of the handlebars should be at the same height as the saddle. If the hip flexion angle is less than 130°, the top of the handlebars should be lower than the saddle, and if the hip flexion is greater that 140°, the top of the handlebars should be higher than the saddle. When the handlebars have been adjusted to the initial height, fine adjustment can be made after riding the bike. For example, if the rider experiences a sore neck or lower back pain, it may be advisable to raise the handlebars. Conversely, if the cyclist does not experience neck or back discomfort but wishes to improve performance, he may lower the handlebars.

It will be appreciated that the invention is not restricted to the particular embodiment that has been described, and that variations may be made therein without departing from the scope of the invention as defined in the appended claims and equivalents thereof. For example, instead of providing the adjustable connecting strip 18, the connecting strip may be of fixed length, adapted to a standard crank length. Also, the stirrup bars need not be connected by flexible attachment elements, since the tool may comprise a stiff, crank shaped structure and a handle attached to stirrup bars extending perpendicularly from a straight connecting bar of length equal to the total length of the crank. Unless the context indicates otherwise, a reference in a claim to the number of instances of an element, be it a reference to one instance or more than one instance, requires at least the stated number of instances of the element but is not intended to exclude from the scope of the claim a structure or method having more instances of that element than stated.

The invention claimed is:

1. A method of measuring hip flexion, including:
   positioning oneself on a substantially flat surface,
   engaging one's right foot with a first stirrup element of a tool that also comprises a second stirrup element, a handle, and attachment elements attaching the first and second stirrup elements to each other and to the handle,
   engaging one's left foot with the second stirrup element,
   positioning oneself so that one's back is against the substantially flat surface, and wherein
   the right leg is substantially fully extended and is directed away from the substantially flat surface,
   the left leg is bent, and
   the left foot is adjacent the right calf,
   grasping the handle, and
   pulling the handle towards one's chest while the right leg remains straight, and
   moving the first stirrup element towards one's head to a position in which one's lumbo/sacral spine area moves away from the substantially flat surface, and
   measuring the hip flexion.

2. A method according to claim 1, wherein the first and second stirrup elements comprise first and second substantially rigid elements and the attachment elements comprise flexible elements that attach the first and second substantially rigid elements to each other.

3. A method of measuring hip flexion of a cyclist, including:
   providing a tool that comprises a first stirrup element, a second stirrup element, a handle, and attachment elements attaching the first and second stirrup elements to each other and to the handle,
   positioning the cyclist so that the cyclist's back is against a substantially flat surface, and wherein
   one leg is extended away from the substantially flat surface,
   the foot of said one leg engages the first stirrup element,
   the other leg is bent, and
   the foot of said other leg engages the second stirrup element,
   grasping the handle and pulling the handle towards the cyclist's chest while said one leg remains straight and
   moving the first stirrup element towards the cyclist's head to a position in which the cyclist's lumbo/sacral spine area moves away from the substantially flat surface, and
   measuring the cyclist's hip flexion.

4. A method according to claim 3, wherein the first and second stirrup elements comprise first and second substantially rigid elements and the attachment elements comprise flexible elements that attach the first and second substantially rigid elements to each other.

5. A method of fitting a bicycle to a cyclist, including:
   providing a tool that comprises a first stirrup element, a second stirrup element, a handle, and attachment elements attaching the first and second stirrup elements to each other and to the handle,
   positioning the cyclist so that the cyclist's back is against a substantially flat surface, and wherein
   one leg is extended away from the substantially flat surface,
   the foot of said one leg engages the first stirrup element,
   the other leg is bent, and
   the foot of said other leg engages the second stirrup element,
   grasping the handle and pulling the handle towards the cyclist's chest while said one leg remains straight and
   moving the first stirrup element towards the cyclist's head to a position in which the cyclist's lumbo/sacral spine area moves away from the substantially flat surface,
   measuring the cyclist's hip flexion, and
   in the event that the cyclist's hip flexion is in the range from about 130° to about 140°, adjusting the bicycle so that the top of the handlebars is level with the saddle;
   in the event that the cyclist's hip flexion is greater than about 140°, adjusting the bicycle so that the top of the handlebars is higher than the saddle;
   in the event that the cyclist's hip flexion is smaller than about 130°, adjusting the bicycle so that the top of the handlebars is lower than the saddle.

6. A method according to claim 5, wherein the first and second stirrup elements comprise first and second substantially rigid elements and the attachment elements comprise flexible elements that attach the first and second substantially rigid elements to each other.

* * * * *